United States Patent [19]
Ozawa et al.

[11] Patent Number: 5,409,709
[45] Date of Patent: Apr. 25, 1995

[54] ANTIPYRETIC ANALGESIC PREPARATION CONTAINING IBUPROFEN

[75] Inventors: Kiyotaka Ozawa, Hadano; Ryoko Sugita, Yokohama; Kiyo Adachi, Kanagawa; Tomiyuki Yanase, Sagamihara; Syuichi Ueda, Odawara; Aya Yamane, Fujisawa, all of Japan

[73] Assignee: Lion Corporation, Tokyo, Japan

[21] Appl. No.: 981,340

[22] Filed: Nov. 25, 1992

[30] Foreign Application Priority Data

Nov. 29, 1991 [JP] Japan ................. 3-356097
Feb. 17, 1992 [JP] Japan ................. 4-079384
Mar. 3, 1992 [JP] Japan ................. 4-094984

[51] Int. Cl.⁶ ............... A61K 9/24; A61K 9/28
[52] U.S. Cl. .................... 424/464; 424/472; 424/474; 424/475; 424/473; 514/819; 514/825; 514/923
[58] Field of Search ........... 424/464, 472, 473, 474, 424/475

[56] References Cited

U.S. PATENT DOCUMENTS 5,053,396 10/1991 Blass ...................... 514/45

FOREIGN PATENT DOCUMENTS 56-97224 8/1981 Japan.
56-154416 11/1981 Japan.
59-104315 6/1984 Japan.
61-134315 6/1986 Japan.
62-292718 12/1987 Japan.
63-101321 5/1988 Japan.
63-198620 8/1988 Japan.
63-258808 10/1988 Japan.
63-301817 12/1988 Japan.
2-286614 11/1990 Japan.

*Primary Examiner*—Thurman K. Page
*Assistant Examiner*—James M. Spear

[57] ABSTRACT

An ibuprofen-containing antipyretic analgesic preparation blending 0.01–30 parts by weight of acetaminophen based on 1 part by weight of ibuprofen, 0.05–100 parts by weight of magnesium-based antacids based on 1 part by weight of the total amount of ibuprofen and acetaminophen, and/or 0.01–30 parts by weight of at least one sedative selected from bromovalerylurea and allylisopropylacetylurea based on 1 part by weight of ibuprofen.

5 Claims, No Drawings

ANTIPYRETIC ANALGESIC PREPARATION CONTAINING IBUPROFEN

BACKGROUND OF THE INVENTION

1. Field of the Invention

The present invention relates to an ibuprofen-containing antipyretic analgesic preparation, and more specifically, it relates to an ibuprofen-containing antipyretic analgesic preparation comprising ibuprofen, acetaminophen and magnesium-based antacids and/or a specific sedative.

2. Description of the Related Art

Numerous antipyretic analgesics are known in the prior art. Examples of those drugs that are widely used include combinations of aniline derivatives such as acetaminophen with salicylic acid derivatives such as aspirin and etoxybenzamide. However antipyretic analgesic preparations of salicylic acid derivatives have the disadvantage of easily causing gastric disorders. Thus, efforts are being made to develop antipyretic analgesic preparations having excellent efficacy and minimal acute toxicity by combining ibuprofen and antipyretic analgesic preparations of aniline derivatives in place of antipyretic analgesic preparations of salicylic acid derivatives (e.g., Japanese Unexamined Patent Publication Nos. 56-97224, 56-154416 and 59-104315).

Ibuprofen demonstrates superior antipyretic, analgesic and anti-inflammatory effects, and is widely used as a non-steroidal drug. However, in the case of oral administration of ibuprofen as well, there are cases of occurrence of feeling of discomfort in the stomach, gastralgia, nausea and so forth in the same manner as antipyretic analgesic preparations of salicylic acid derivatives, and the occurrence of gastric disorders has been indicated as a side effect of such preparations.

Consequently, combining the use of these preparations with salicylic acid derivatives (e.g., Japanese Unexamined Patent Publication No. 61-134315) or antacids and/or mucosal protective agents (e.g., Japanese Unexamined Patent Publication No. 63-198620) has been proposed for the purpose of relieving gastric disorders caused by oral administration of ibuprofen. However, the antipyretic analgesic preparations containing the drugs mentioned above were not always able to satisfy both antipyretic analgesic effects and relief of gastric disorders.

As stated above, although antacids are important ingredients that suppress the side effects of ibuprofen, the manufacturing of preparations of ibuprofen and antacids is difficult due to the occurrence of remarkable changes by the combination. Generally, in the case of pharmaceutical manufacturing preparations of ingredients in which compatibility changes occur, a method is used wherein layered tablets, press-coated tablets and each ingredient are coated with saccharide or polymer films (Japanese Unexamined Patent Publication No. 2-286614). However, in the case of simply layering or press-coat blending of ibuprofen, antacids and acetaminophen, there are disadvantages including being unable to prevent coloring and fusion of each ingredient at the interfaces, reduced content of ibuprofen, and unpleasant odor and taste.

In addition, manufacturing methods wherein ibuprofen, antacids and acetaminophen are separately coated with saccharides or polymer films require considerable processing time and are expensive due to the need for raw materials for the coating agent. Moreover, these methods also have the disadvantages of disintegration and elution of each ingredient due to the coating, along with incomplete separation of each ingredient due to partial destruction of the coating due to compression molding (tableting) in the case of tablet production.

On the other hand, examples of methods known in the prior art for prolonging the effects of drugs include:

(1) Methods which extend the disintegration properties of the preparation in the form of lozenges, pills and so forth;

(2) Methods which form multi-layer coated tablets by sugar coating the outside layer of the tablet and applying an enteric coating to the inside layer by means of a film coating;

(3) Methods which form spansule capsules in which capsules are filled with granules having different disintegration times;

(4) Methods which form span tab types in which granules having different disintegration times are formed into tablets;

(5) Methods which form spantabs, multi-layered spantabs in which fast-releasing granules and slow-releasing granules are divided and formed into tablets with two or three layers; and, (6) Methods which form tablets in which the release of medication is controlled by a polymer matrix. However, although these prolonged-action pharmaceuticals are improved in terms of increased duration of the medication, they also have disadvantages including (1) insufficient fast-acting properties, (2) a complex manufacturing process, and (3) difficulties in stabilization of ingredients.

SUMMARY OF THE INVENTION

Accordingly, the objects of the present invention are to eliminate the disadvantages of the antipyretic analgesic preparations of the prior art mentioned above, such as the causing of gastric disorders, and provide an antipyretic analgesic preparation having both excellent analgesic action and antipyretic action as well as a high degree of safety.

In addition, another object of the present invention is to eliminate disadvantages such as the short duration of activity of ibuprofen, and provide an antipyretic analgesic preparation having excellent anti-inflammatory, analgesic and antipyretic action.

Moreover, a further object of the present invention is stably blend ibuprofen, antacids and acetaminophen to prevent changes in appearance (coloring and fusion).

In accordance with the present invention, there is provided an ibuprofen-containing antipyretic analgesic preparation which inhibits gastric disorders and synergistically improves antipyretic analgesic action, comprising ibuprofen, acetaminophen and magnesium-based antacids, wherein the acetaminophen content is 0.01–30 parts by weight based upon 1 part by weight of ibuprofen, and the magnesium-based antacids content is 0.05–100 parts by weight based on 1 part by weight of the total amount of ibuprofen and acetaminophen.

In accordance with the present invention, there is also provided an ibuprofen-containing antipyretic analgesic preparation which extends the duration of activity and synergistically improves antipyretic analgesic action by blending ibuprofen, acetaminophen and a sedative in the form of bromovalerylurea and/or allylisopropylacetylurea (and, optionally, magnesium-based antacids).

In accordance with the present invention, there is further provided an ibuprofen-containing antipyretic analgesic preparation comprising a layer containing ibuprofen as the main ingredient, a layer containing magnesium-based antacids as the main ingredient, and at least one layer between the above layers that does not contain both of the above ingredients, wherein acetaminophen is contained in layers other than the layer containing antacids as the main ingredient.

DESCRIPTION OF THE PREFERRED EMBODIMENT

Examples of the ibuprofen usable in the present invention include ibuprofen (2-(4-isobutyl phenyl)propionic acid) and its salts. This compound can usually be blended into the composition in the amount of 0.1–99% by weight, and preferably 1.0–90% by weight.

The acetaminophen (N-(4-hydroxyphenyl)acetamide) used in the present invention can be blended in an amount of 0.01–30 parts by weight, and preferably 0.1–20 parts by weight, based on 1 part by weight of ibuprofen. When the amount blended is out of this range, it is difficult to demonstrate the synergistic effect mentioned above.

Examples of the magnesium-based antacid used in the present invention include magnesium silicate, magnesium oxide, magnesium hydroxide, magnesium carbonate, exissicated mixed aluminum hydroxide and magnesium carbonat gel, coprecipitate of aluminum hydroxide, calcium carbonate and magnesium carbonate, magnesium metasilicate aluminate, magnesium aluminosilicate, and the coprecipitate of magnesium hydroxide and potassium aluminum sulfate. Particularly preferable examples of magnesium-based antacids include magnesium oxide and magnesium carbonate. In the present invention, one type of these antacids may be used together with the ibuprofen, or two or more types may be used together with the ibuprofen.

These antacids can be blended in an amount of 0.05–100 parts by weight, and preferably 0.1–50 parts by weight, based on 1 part by weight of the total amount of ibuprofen and acetaminophen. When this amount is less than 0.05 parts by weight, gastric disorders are not relieved and antipyretic analgesic effects are not improved. On the other hand, when this amount is more than 100 parts by weight, there is a risk of the appearance of side effects of magnesium-based antacids and the quantity becomes higher.

Examples of sedatives usable in the present invention include bromovalerylurea (2-bromo-3-methyl buturylurea and allylisopropylacetylurea (N-(aminocarbonyl)-2-(1-methylethyl)-4-pentenamide). In the present invention, at least one type of these sedatives is used together with the ibuprofen. These sedatives can be blended in an amount of 0.05–100 parts by weight, and preferably 0.1–10 parts by weight, based on 1 part by weight of ibuprofen. When this blending amount is less than 0.05 parts by weight, antipyretic analgesic effects are not improved and acting time is not extended. When this amount is more than 100 parts by weight, the effects of ibuprofen are not adequately demonstrated.

The antipyretic analgesic preparation according to the present invention can also contain, as necessary, antihistaminics such as isothipendyl hydrochloride, diphenylpyraline hydrochloride, diphenhydramine hydrochloride difeterol hydrochloride, triprolidine hydrochloride, tripelennamine hydrochloride, thonzylamine hydrochloride, fenethazine hydrochloride, methdilazine hydrochloride, diphenhydramine salicylate, carbinoxamine diphenyldisulfonate, alimemazine tartrate, diphenhydramine tannate, diphenylpyraline chlorotheophyllinate, mebhydrolin napadisylate, promethazine methylene disalicylate, carbinoxamine maleate, dl-chlorpheniramine maleate, d-chlorpheniramine maleate and difeterol phosphate; central nervous system stimulants such as caffeine and sodium benzoate, caffeine and anhydrous caffeine; and, vitamin preparations such as vitamin $B_1$, its derivatives and their salts, vitamin $B_2$, its derivatives and their salts, vitamin C, its derivatives and their salts, and hesperidine, its derivatives and their salts.

The antipyretic analgesic preparation of the present invention is effective against pain, such as headache, toothache, pain after tooth extraction, sore throat, earache, arthralgia, neuralgia, lumbago, muscular pain and menstrual pain, relief of fever due to ague or pyrexia.

In addition, the antipyretic analgesic preparation of the present invention can be administered orally to ordinal adults in the amount of 100–6000 mg as the total amount of ibuprofen, acetaminophen and magnesium-based antacids and/or bromovalerylurea or allylisopropylacetylurea in a single or multiple administrations per day. This dose can be suitably increased or decreased according to the age, body weight and symptoms of the patient.

Moreover, the antipyretic analgesic preparation of the present invention is used in various forms including tablets, granules, powders, capsules and syrups. These preparations can be prepared by any conventional methods. Examples of those ingredients usable in the preparation of solid preparations include vehicles such as lactose, starch, sucrose, mannitol and crystalline cellulose; binders such as hydroxypropylcellulose, carboxymethylcellulose, gelatin, carboxymethylcellulose-sodium and Acasia; disintegrants such as carboxymethylcellulose-calcium, polyvinylpyrrolidone or its crosslinked form and lower substituted hydroxypropylcellulose; non-ionic surfactants such as sucrose esters of fatty acids, polyoxysorbitan fatty acid ester; tablet lubricants such as calcium stearate, magnesium stearate, dimethylpolysiloxane, talc, polyethylene glycol and hydrogenated oil; and, optionally other colorants and sweetening agents. In addition, said preparations can be coated, if necessary. Examples of coating agents include hydroxypropylcellulose, hydroxypropylmethylcellulose, Eudragit (Röhm Pharma.), polyvinylpyrrolidone, polyethylene glycol, shellac, methylcellulose, ethylcellulose, cellulose acetate phthalate and hydroxypropylcellulose phthalate. Said preparations can also be given a sugar coating having a main ingredient such as sucrose, Acasia calcium carbonate, talc or gelatin.

Examples of ingredients usable in the preparation of liquid preparations include purified water, ethanol, glycerin, sucrose, propylene glycol, polyethylene glycol, polyoxyethylene sorbitan fatty acid ester, aluminum metahydroxide, agar and tragacanth. Other solubility adjuvants, buffering agents, antimicrobial preservatives, flavoring agents, colorants and agents to add taste and odor can also be optionally used.

In the present invention, although the dosage form may be that of a layered preparation having at least three layers by providing a layer containing ibuprofen as the main ingredient and not containing antacids, a layer containing antacids as the main ingredient and not containing ibuprofen, and at least one layer not containing ibuprofen and antacids between the above two layers, and also by blending acetaminophen in any layer other than the layer containing antacids, preferably, the layer is provided containing antacids by means of at least one layer not containing both ibuprofen and acetaminophen.

In addition, the stability during storage of the resulting layered preparation can be further improved and unpleasant odor and taste can be eliminated by additionally coating said layered preparation with a coating agent.

Examples of such coating agents usable in the present invention include hydroxypropylcellulose, hydroxypropylmethylcellulose, Eudragit (Röhm Pharma.), polyvinylpyrrolidone, macrogol, shellac, methylcellulose, ethylcellulose, cellulose acetate phthalate, hydroxypropylcellulose phthalate, sucrose, Acasia, calcium carbonate, talc, gelatin, glycerin, propylene glycol, triacetin, acetylated monoglyceride, citrate esters, glycerine fatty acid ester, pigments and dyes (aluminum lake, titanium oxide, iron oxide, carotene), crystalline cellulose, lactose, starch, magnesium stearate, talc and carboxymethylcellulose. Film coatings, sugar coatings and dry coatings can be applied having the above substances as their main ingredients.

As indicated above, the ibuprofen-containing antipyretic analgesic preparation of the present invention has excellent antipyretic analgesic action, relieves the gastric disorder effects of ibuprofen, and demonstrates a high degree of safety in use. Moreover, as a result of blending in a specific sedative mentioned above, in addition to demonstrating superior antipyretic analgesic action, the addition effect is obtained in which the effects are sustained for an extended period of time.

In addition, the layered preparation containing ibuprofen, antacids and acetaminophen of the present invention is stable without individually coating each ingredient with a coating agent as a result of each ingredient being in the form of layers. Thus, remarkable changes in appearance due to changes in blending of each of these ingredients is suppressed, allowing the manufacturing of a preparation that demonstrates an extremely low level of changes in quality with the elapse of time. Moreover, changes in quality with the elapse of time can be further prevented by coating plain tablets. This serves to significantly improve the unpleasant odor and taste of ibuprofen, as well as to improve the ease of taking such preparations. Moreover, since the preparation of the present invention does not require that the ibuprofen, antacids and acetaminophen individually coated with a coating agent, the advantages of shortening the time required for manufacturing the preparation and allowing faster elution time of each ingredient are obtained.

EXAMPLES

The present invention will now be further illustrated by, but is by no means limited to, the following Examples.

Example 1—1 (Gastric Disorder Effects)

Six-week-old SD strain male rats (body weights: 130-150 g) were used in the experiment divided into groups of 7-10 animals each. After fasting the animals for 24 hours, each of the test medications was orally administered to the animals of each group at a volume of 1.0 ml/100 g B.W. Four hours later, the stomachs of the animals were extracted. After fixing with 2% formalin, a vertical incision was made along the greater curvature. The specimens were observed using a stereoscopic microscope and evaluated for the presence of disorders of the gastric mucosa to determine the rate of occurrence of ulcers.

The test medications were used by suspending in 5% Acasia solution at the time of use.

The 50% ulcerogenic dose ($UD_{50}$) was calculated according to the Litchfield & Wilcoxon method. Those results are indicated in Table 1. The values are represented in the terms of the amount of ibuprofen in each medication.

TABLE 1-1

| Gastric Disorder Effects | |
|---|---|
| Medication (weight ratio) | $UD_{50}$ (mg/kg) |
| Ibuprofen | 34.4 |
| Ibuprofen + acetaminophen (1:1) | 19.8 |
| Ibuprofen + acetaminophen + magnesium oxide (1:1:2.2) | 218 |
| Ibuprofen + acetaminophen + magnesium carbonate + magnesium oxide (1:1:1.6:0.6) | 210 |

In comparison with administration of ibuprofen alone, blending of ibuprofen with acetaminophen, which does not cause gastric disorders, resulted in a lowering of the $UD_{50}$ value. In contrast, when magnesium-based antacids were blended into the ibuprofen and acetoaminophen, the occurrence of gastric disorders was inhibited remarkably.

Example 1-2 (Analgesic Action)

Five-week-old ddY strain male mice (body weights: 20-25 g) were used in the experiment divided into groups of 19-25 animals each.

Each of the test medications was administered orally to the animals in each of the groups at a volume of 0.1 ml/10 g B.W. After 60 minutes, 0.7% acetic acid was administered intraperitoneally at the volume of 0.1 ml/10 g B.W. The number of writhing syndrome was then immediately measured for 20 minutes. The rate of inhibition was then calculated according to the following formula from the measured number of writhing syndrome and the number of writhing syndrome of a control group (orally administered with 1% carboxymethylcellulose not containing the test medication). The $ED_{50}$ was then determined based on this rate of inhibition.

Rate of Inhibition (%) =

$$\frac{\text{Number of writhing syndrome of control group} - \text{Number of writhing syndrom of test group}}{\text{Number of writhing syndrom of control group}} \times 100$$

The test medications were used by suspending in a 1% carboxymethylcellulose solution at the time of use. The 50% effective dose ($ED_{50}$) was calculated according to the Litchfield & Wilcoxon method. Those results are indicated in Table 1-2. The values are indicated in terms of the amount of analgesic antipyretic ingredient.

TABLE 1-2

| Analgesic Action | |
|---|---|
| Medication (weight ratio) | $ED_{50}$ (mg/kg) |
| Ibuprofen | 137.0 |
| Ibuprofen + acetaminophen (1:1) | 70.3 |
| Ibuprofen + acetaminophen + magnesium oxide (1:1:2.2) | 21.9 |

TABLE 1-2-continued

| Analgesic Action | |
|---|---|
| Medication (weight ratio) | $ED_{50}$ (mg/kg) |
| Ibuprofen + acetaminophen + magnesium carbonate + magnesium oxide (1:1:1.6:0.6) | 30.0 |

The blending of acetaminophen, an antipyretic analgesic, with ibuprofen resulted in the $ED_{50}$ value being reduced to 51% of that of ibuprofen alone, thus enhancing the analgesic action upon the pharmacological potentiation.

By simultaneously blending ibuprofen with acetaminophen and magnesium-based antacid, which in itself does not have analgesic action, the $ED_{50}$ value was reduced to roughly 31–43% of the ibuprofen and acetaminophen, thus indicating remarkable enhancement of analgesic action.

Example 1-3 (Antipyretic Action)

Eight-week-old Wistar strain male rats (body weights: 200–240 g) were used in the experiment divided into groups of 5–7 animals each.

After twice measuring the body temperatures of the animals at 30 minute intervals, a 7.5% yeast solution was administered subcutaneously at a volume of 1.0 ml/100 g B.W. Three hours later, each of the test medications was administered orally to the animals of each group at a volume of 0.5 ml/100 g B.W. Body temperatures were then measured six times thereafter at one hour intervals. The pyrogenic area up to 6 hours by dividing that of the control group. The $ED_{50}$ values were then determined from that rate of inhibition.

The test medications were used by suspending in a 5% Acasia solution of Arabic gum at the time of use.

The 50% effective dose ($ED_{50}$) was calculated according to the Litchfield & Wilcoxon method. Those results are indicated in Table 1-3. The values are indicated in terms of the amount of the antipyretic analgesic ingredient.

TABLE 1-3

| Antipyretic Action | |
|---|---|
| Medication (weight ratio) | $ED_{50}$ (mg/kg) |
| Ibuprofen | 20.4 |
| Ibuprofen + acetaminophen (1:1) | 10.5 |
| Ibuprofen + acetaminophen + magnesium oxide (1:1:2.2) | 3.3 |
| Ibuprofen + acetaminophen + magnesium carbonate + magnesium oxide (1:1:1.6:0.6) | 4.5 |

By blending acetaminophen with ibuprofen, the $ED_{50}$ value decreased to 51% of that of ibuprofen alone, indicating enhancement of antipyretic action upon the pharmaceutical potentiation.

Moreover, by simultaneously blending with magnesium-based antacids, the $ED_{50}$ value decreased remarkably lower than that of the ibuprofen and acetaminophen, and gastric disorders were also suppressed.

The analgesic action, antipyretic action and gastric disorder effects in the following embodiments and comparative examples were evaluated using procedures similar to those of Examples 1—1 through 1-3 described above. Tablets were crushed and hard and soft capsules were used after removing the contents, then they were suspended in a solvent. The values are indicated in the amounts of the respective preparations. Values for hard and soft capsules are indicated in terms of the amounts of the contents.

Example 1-4 (Evaluation)

TABLE 1-4

| Composition of a Single Tablet | |
|---|---|
| Blended Ingredients | Blended Amount (mg) |
| Ibuprofen | 65 |
| Acetaminophen | 65 |
| Magnesium oxide | 50 |
| Magnesium carbonate | 100 |
| Hydroxypropylcellulose | 6 |
| Crystalline cellulose | 50 |
| Corn starch | 10 |
| Carboxymethylcellulose | 20 |
| Magnsesium stearate | 3 |
| Total | 369 |

The ingredients described in Table 1-4 were formed into tablets using a rotary tablet forming machine to obtain the tablet preparation. The evaluation results are indicated below.

| | |
|---|---|
| Analgesic action | $ED_{50}$: 85.4 mg/kg |
| Antipyretic action | $ED_{50}$: 12.8 mg/kg |
| Gastric disorder effects | $UD_{50}$: The rate of occurrence of ulcers was 30% at a dose of 1000 mg/kg for which administration was possible. |

Example 1-5 (Evaluation)

TABLE 1-5

| Composition of a Single Tablet | |
|---|---|
| Blended Ingredients | Blended Amount (mg) |
| Ibuprofen | 70 |
| Acetaminophon | 35 |
| Magnesium carbonate | 100 |
| Aluminum glycinate | 50 |
| Gelatin | 5 |
| Polyvinylpyrrolidone | 13 |
| Corn starch | 17 |
| Croscarmelose | 10 |
| Magnesium stearate | 3 |
| Total | 303 |

The ingredients described in Table 1-5 were formed into tablets using a rotary tablet forming machine to obtain the tablet preparation. The evaluation results are indicated below.

| | |
|---|---|
| Analgesic action | $ED_{50}$: 171.9 mg/kg |
| Antipyretic action | $ED_{50}$: 23.5 mg/kg |
| Gastric disorder effects | $UD_{50}$: The rate of occurrence of ulcers was 20% at a dose of 1000 mg/kg for which administration was possible. |

Example 1-6 (Evaluation)

TABLE 1-6

| Composition of a Single Packet | |
|---|---|
| Blended Ingredients | Blended Amount (mg) |
| Ibuprofen | 120 |
| Acetaminophen | 90 |
| Magnesium oxide | 100 |
| Synthetic hydrotalcite | 270 |
| Allylisopropylacetylurea | 60 |
| Caffeine | 90 |
| Pregelatinized starch | 35 |
| Corn starch | 15 |

TABLE 1-6-continued

Composition of a Single Packet

| Blended Ingredients | Blended Amount (mg) |
|---|---|
| Total | 775 |

The ingredients described in Table 1-6 were formed into granules by extrusion granulation to obtain a granular preparation, followed by drying and grading. The evaluation results are indicated below.

| | |
|---|---|
| Analgesic action | $ED_{50}$: 106.0 mg/kg |
| Antipyretic action | $ED_{50}$: 15.9 mg/kg |
| Gastric disorder effects | $UD_{50}$: The rate of occurrence of ulcers was 30% at a dose of 1000 mg/kg for which administration was possible. |

Example 1-7 (Evaluation)

TABLE 1-7

Composition of a Single Packet

| Blended Ingredients | Blended Amount (mg) |
|---|---|
| Ibuprofen | 60 |
| Acetaminophen | 120 |
| Magnesium silicate | 500 |
| Acasia | 5 |
| Corn starch | 20 |
| Total | 705 |

The ingredients described in Table 1-7 were formed into granules by extrusion granulation to obtain a granular preparation, followed by drying and grading. The evaluation results are indicated below.

| | |
|---|---|
| Analgesic action | $ED_{50}$: 231.0 mg/kg |
| Antipyretic action | $ED_{50}$: 34.5 mg/kg |
| Gastric disorder effects | $UD_{50}$: The rate of occurrence of ulcers was 10% at a dose of 1000 mg/kg for which administration was possible. |

Example 1-8 (Evaluation)

TABLE 1-8

Composition of a Single Packet

| Blended Ingredients | Blended Amount (mg) |
|---|---|
| Ibuprofen | 130 |
| Acetaminophen | 50 |
| Magnesium carbonate | 100 |
| Magnesium metasilicate aluminate | 200 |
| Bromovalerylurea | 200 |
| Caffeine | 80 |
| Hydroxypropylcellulose | 25 |
| Total | 960 |

The ingredients described in Table 1-8 were formed into granules to obtain a powder. The evaluation results are indicated below.

| | |
|---|---|
| Analgesic action | $ED_{50}$: 180.5 mg/kg |
| Antipyretic action | $ED_{50}$: 25.2 mg/kg |
| Gastric disorder effects | $UD_{50}$: The rate of occurrence of ulcers was 20% at a dose of 1000 mg/kg for which administration was possible. |

Example 1-9 (Evaluation)

TABLE 1-9

Composition of a Single Capsule

| Blended Ingredients | Blended Amount (mg) |
|---|---|
| Ibuprofen | 50 |
| Acetaminophen | 50 |
| Magnesium silicate | 200 |
| Carboxymethylcellulose | 50 |
| Hydrogenated oil | 30 |
| Total | 390 |

The ingredients described in Table 1-9 were mixed to obtain a hard capsule according to common methods. The evaluation results are indicated below.

| | |
|---|---|
| Analgesic action | $ED_{50}$: 123.2 mg/kg |
| Antipyretic action | $ED_{50}$: 15.4 mg/kg |
| Gastric disorder effects | $UD_{50}$: The rate of occurrence of ulcers was 20% at a dose of 1000 mg/kg for which administration was possible. |

Example 1-10 (Evaluation)

TABLE 1-10

Composition of a Single Capsule

| Blended Ingredients | Blended Amount (mg) |
|---|---|
| Ibuprofen | 60 |
| Acetaminophen | 30 |
| Magnesium carbonate | 100 |
| Vitamin $B_1$ | 8 |
| Corn starch | 22 |
| Magnesium stearate | 2 |
| Total | 222 |

The ingredients described in Table 1-10 were mixed to obtain a hard capsule according to common methods. The evaluation results are indicated below.

| | |
|---|---|
| Analgesic action | $ED_{50}$: 215.4 mg/kg |
| Antipyretic action | $ED_{50}$: 26.9 mg/kg |
| Gastric disorder affects | $UD_{50}$: The rate of occurrence of ulcers was 30% at a dose of 1000 mg/kg for which administration was possible. |

Example 1-11 (Evaluation)

TABLE 1-11

Composition of a Single Capsule

| Blended Ingredients | Blended Amount (mg) |
|---|---|
| Ibuprofen | 60 |
| Acetoaminophen | 65 |
| Magnesium oxide | 50 |
| Safflower oil | 200 |
| dl-tocopherol | 5 |
| Total | 390 |

The ingredients described in Table 1-11 were mixed to obtain a soft capsule according to common methods. The evaluation results are indicated below.

| | |
|---|---|
| Analgesic action | $ED_{50}$: 96.6 mg/kg |
| Antipyretic action | $ED_{50}$: 12.4 mg/kg |

| Gastric disorder effects | UD$_{50}$: 236 mg/kg |
|---|---|

Example 2-1 (Analgesic Action)

Wistar strain male rats (body weights: 130–160 g) were used in the experiment divided into groups of 7–11 animals each. Test medication A consisted of a suspension of Acasia used as the control. The other test medications contained the ingredients listed in the Table below, and were suspended in Acasia solution. These test medications were administered orally at a volume of 1 ml/100 g B.W. A pressure stimulation device (Analgesy-meter Model TK-201, Unicom) was used to apply pressure to the base of the tails of the animals. A pain threshold of 60–80 mgHg was selected for the experimented animal based on parameters of reaction to temporary pain consisting of writhing, fleeing and squealing. The pain threshold was measured prior to oral administration of each test medication as well as at 30 and 120 minutes after administration. The ratio of the rise in the pain threshold at 30 and 120 minutes after administration was calculated from comparison with that before administration.

As a result, although a remarkable rise was observed at 30 minutes for test medication B (ibuprofen alone), the pain threshold was essentially equal to that before administration at 120 minutes. On the other hand, in the case of test medication C and D, the pain threshold rose higher than test medication B at 30 minutes, and a remarkable rise was also observed at 120 minutes, thus indicating an extension of the time during which analgesic effects by the sedative are sustained.

TABLE 2-1

| Rise Ratio of Pain Threshold for Test Medications | | |
|---|---|---|
| | After Administration | |
| Test Medication | 30 Minute Value (%) | 120 Minute Value (%) |
| A | 0 | 0 |
| B | 27 | 6 |
| C | 57 | 27 |
| D | 46 | 15 |

Explanation of symbols in table:
A: Acasia (control)
B: Ibuprofen (200 mg/kg)
C: Ibuprofen (100 mg/kg) + acetaminophen (100 mg/kg) + bromovalerylurea (150 mg/kg)
D: Ibuprofen (100 mg/kg) + acetaminophon (100 mg/kg) + allylisopropylacetylurea (50 mg/kg)

Example 2—2 (Analgesic Action)

Tablets containing the ingredients listed in Table 2—2 below were crushed in a mortar, suspended in Acasia solution and administered orally at a dose of 100 mg/kg as ibuprofen. The rise ratio of the pain threshold was evaluated in the same manner as Example 2-1, and those results are indicated in Table 2-3 below.

Remarkable rises in pain threshold in comparison with ibuprofen alone were observed at both 30 and 120 minutes after administration, and extension of those effects by the sedative was also observed.

TABLE 2-2

| Blended Ingredients (in 1 tablet) | Blended Amount (mg) |
|---|---|
| Ibuprofen | 70 |
| Acetaminophen | 70 |
| Allylisopropylacetylurea | 30 |
| Anhydrous caffeine | 40 |
| Magnesium oxide | 50 |

TABLE 2-2-continued

| Blended Ingredients (in 1 tablet) | Blended Amount (mg) |
|---|---|
| Gelatin | 5 |
| Polyvinylpyrrolidone | 13 |
| Corn starch | 12 |
| Croscarmelose | 10 |
| Magnesium stearate | 3 |

TABLE 2-3

| 30 minutes after administration of test medication | 58% |
|---|---|
| 120 minutes after administration of test medication | 21% |

Example 2-3 (Analgesic Action)

The contents were removed from hard capsules containing the ingredients listed in Table 2-4, crushed with a mortar, suspended in Acasia solution and administered orally at a dose of 100 mg/kg as ibuprofen. The rise ratio of the pain threshold was evaluated in the same manner as Example 2-1, and those results are indicated in Table 2-5 below.

A remarkable rise was observed in the pain threshold at both 30 minutes and 120 minutes after administration in comparison with administration of ibuprofen alone, and extension of those effects by the sedative was also observed.

TABLE 2-4

| Hard Capsule Blended Ingredients (1 capsule) | Blended Amount (mg) |
|---|---|
| Ibuprofen | 50 |
| Acetaminophen | 50 |
| Bromovalerylurea | 100 |
| Anhydrous caffeine | 40 |
| Magnesium silicate | 200 |
| Ac—Di—Sol (Azahi Chemical) | 50 |
| Hydrogenated oil | 30 |

TABLE 2-5

| 30 minutes after administration of test medication | 62% |
|---|---|
| 120 minutes after administration of test medication | 20% |

Example 3-1 (Stabilized Blend)

180 g of crystalline cellulose is added to 390 g of ibuprofen, followed by granulation in an aqueous solution of hydroxypropylcellulose (Freund, Spir a flow model SFC-MINI). 485 g of these granules are weighed, followed by the addition of 100 g of carboxymethylcellulose and 3 g of magnesium stearate to produce the first layer.

390 g of acetoaminophen and 180 g of allylisopropylacetylurea are added, followed by granulation in an aqueous solution of hydroxypropylcellulose (Freund, Spir a flow model SFC-MINI). 485 g of these granules are weighed, followed by the addition of 200 g of anhydrous caffeine, 100 g of carboxymethylcellulose and 4 g of magnesium stearate to produce the second layer.

Water is added to 300 g of magnesium oxide, 300 g of magnesium carbonate and 120 g of pregelatinized starch followed by granulation (Fukae Powtec, High-Speed Mixer model FS-5). After drying and grading, 600 g of these granules are weighed, followed by the addition of 3 g of magnesium stearate to produce the third layer.

The above-mentioned first through third layers are gradually transferred to a die and formed into tablets to obtain a non-coated layered preparation having the prescription indicated in Table 3-1 below per tablet.

In addition, 1000 g of these tablets are removed and coated with a 4% film with the coating liquid indicated in Table 3-2 below (Freund, Hi-Coater model 300) to obtain a coated layered preparation.

TABLE 3-1

| Blend Composition of Layered Preparation | |
|---|---|
| Blended Ingredients | Blended Amount (mg) |
| First Layer | |
| Ibuprofen | 65 |
| Crystalline cellulose | 30 |
| Hydroxypropylcellulose | 2 |
| Carboxymethylcellulose | 20 |
| Magnesium stearate | 0.6 |
| Second Layer | |
| Aceatoaminophen | 65 |
| Anhydrous caffeine | 40 |
| Allylisopropylacetylurea | 30 |
| Hydroxypropylcellulose | 2 |
| Carboxymethylcellulose | 20 |
| Magnesium stearate | 0.8 |
| Third Layer | |
| Magnesium oxide | 50 |
| Magnesium carbonate | 50 |
| Pregelatinized starch | 20 |
| Magnesium stearate | 0.6 |
| Total | 396 |

TABLE 3-2

| Film Coating Liquid Blend Composition | |
|---|---|
| Blended Ingredients | Blended Amount (g) |
| Hydroxypropylmethylcellulose | 6.0 |
| Macrogorl 6000 | 1.2 |
| Titanium oxide | 0.6 |
| Talc | 1.2 |
| Water | 91.0 |
| Total | 100.0 |

Example 3-2 (Stabilized Blend)

125 g of corn starch is added to 325 g of ibuprofen and 325 g of acetaminophen. After kneading with an aqueous solution of hydroxypropylcellulose (Ishiyama Shoten, Kneader), the product is dried and graded, followed by the addition of 3.2 g of magnesium stearate to 626 g of this product to produce the first layer.

500 g of directly compressive lactose are added to 400 g of anhydrous caffeine and 300 g of allylisopropylacetyl urea followed by mixing and the addition of 12 g of magnesium stearate to produce the second layer.

120 g of corn starch are added to 600 g of magnesium carbonate, followed by granulation with a gelatin solution (Fukae Powtec, High-Speed Mixer model FS-5). After drying and grading, 620 g of the granules are removed followed by the addition of 3 g of magnesium stearate to produce the third layer.

The above-mentioned first through third layers are gradually transferred to a die and formed into tablets to obtain a non-coated layered preparation having the prescription indicated in Table 3-3 below per tablet.

In addition, 1000 g of these tablets are removed and coated with a 4% film with the coating liquid indicated in Table 3-4 below (Freund, Hi-Coater model 300) to obtain a coated layered preparation.

TABLE 3-3

| Blend Composition of Layered Preparation | |
|---|---|
| Blended Ingredients | Blended Amount (mg) |
| First Layer | |
| Ibuprofen | 65 |
| Acetaminophen | 65 |
| Corn starch | 25 |
| Hydroxypropylcellulose | 1.5 |
| Magnesium stearate | 0.8 |
| Second Layer | |
| Anhydrous caffeine | 40 |
| Allylisopropylacetylurea | 30 |
| Lactose | 50 |
| Magnesium stearate | 1.2 |
| Third Layer | |
| Magnesium carbonate | 100 |
| Gelatin | 4 |
| Corn starch | 20 |
| Magnesium stearate | 0.6 |
| Total | 403.1 |

TABLE 3-4

| Film Coating Liquid Blend Composition | |
|---|---|
| Blended Ingredients | Blended Amount (g) |
| Hydroxypropylmethylcellulose | 8.0 |
| Macrogol 6000 | 1.6 |
| Titanium oxide | 0.8 |
| Talc | 1.6 |
| Water | 88.0 |
| Total | 100.0 |

Example 3—3 (Stabilized Blend)

240 g of crystalline cellulose are added to 390 g of ibuprofen and 180 g of allylisopropylacetylurea followed by granulation with an aqueous solution of hydroxypropylcellulose (Freund, Spir a flow model SFC-MINI). 690 g of these granules are weighed followed by the addition of 100 g of carboxymethylcellulose and 4 g of magnesium stearate to produce the first layer.

325 g of acetaminophen, 200 g of anhydrous caffeine, 300 g of crystalline cellulose, 100 g of carboxymethylcellulose and 5 g of magnesium stearate are mixed to produce the second layer.

600 g of magnesium oxide and 120 g of pregelatinized starch are mixed followed by granulation with a gelatin solution (Ishiyama Shoten, Kneader). After drying and grading, 610 g of these granules are weighed followed by the addition of 3 g of magnesium stearate and mixing to produce the third layer.

The above-mentioned first through third layers are gradually transferred to a die and formed into tablets to obtain a non-coated layered preparation having the prescription indicated in Table 3-5 below per tablet.

In addition, 1000 g of these tablets are removed and coated with a 4% film with the coating liquid indicated in Table 3-6 below (Freund, Hi-Coater model 300) to obtain a coated layered preparation.

TABLE 3-5

| Blend Composition of Layered Preparation | |
|---|---|
| Blended Ingredients | Blended Amount (mg) |
| First Layer | |
| Ibuprofen | 65 |
| Allylisopropylacetylurea | 30 |
| Crystalline cellulose | 40 |
| Hydroxyropylcellulose | 3 |
| Carboxymethylcellulose | 20 |
| Magnesium stearate | 0.8 |

TABLE 3-5-continued

| Blend Composition of Layered Preparation | |
|---|---|
| Blended Ingredients | Blended Amount (mg) |
| Second Layer | |
| Acetaminophen | 65 |
| Anhydrous caffeine | 40 |
| Crystalline cellulose | 60 |
| Carboxymethylcellulose | 20 |
| Magneisum stearate | 1 |
| Third Layer | |
| Magnesium oxide Gelatin | 100 |
| Pregelatinized starch | 20 |
| Magnesium stearate | 0.6 |
| Total | 467.4 |

TABLE 3-6

| Film Coating Liquid Composition | |
|---|---|
| Blended Ingredients | Blended Amount (g) |
| Hydroxypropylmethylcellulose | 6.0 |
| Glycerine fatty acid ester | 1.2 |
| Titanium oxide | 0.6 |
| Ethanol | 79.37 |
| Water | 13.93 |
| Total | 100.0 |

Examples 3-4 (Stabilized Blend)

120 g of crystalline cellulose are added to 390 g of ibuprofen and 390 g of acetaminophen followed by granulation with an aqueous solution of hydroxypropylcellulose (Freund, Spir a flow model SFC-MINI). 765 g of these granules are weighed followed by the addition of 150 g of carboxymethylcellulose and 5 g of magnesium stearate and mixing to produce the first layer.

1 g of magnesium stearate is added to 300 g of crystalline cellulose followed by mixing to produce the second layer.

Water is added to 300 g of magnesium oxide, 300 g of magnesium carbonate, 60 g of corn starch and 180 g of pregelatinized starch followed by granulation (Fukae Powtec, High-Speed Mixer model FS-5). After drying and grading, 700 g of these granules are weighed followed by the addition of 200 g of anhydrous caffeine, 150 g of allylisopropylacetylurea and 5 g of magnesium stearate to produce the third layer.

The above-mentioned first through third layers are gradually transferred to a die and formed into tablets to obtain a non-coated layered preparation having the prescription indicated in Table 3-7 below per tablet.

In addition, 1000 g of these tablets are removed and coated with a 4% film with the coating liquid indicated in Table 3-8 below (Freund, Hi-Coater model 300) to obtain a coated layered preparation.

TABLE 3-7

| Blend Composition of Layered Preparation | |
|---|---|
| Blended Ingredients | Blended Amount (mg) |
| First Layer | |
| Ibuprofen | 65 |
| Acetaminophen | 65 |
| Crystalline cellulose | 20 |
| Hydroxypropylcellulose | 3 |
| Caxboxymethylcellulose | 30 |
| Magnesium stearate | 1 |
| Second Layer | |
| Crystalline cellulose | 30 |
| Magnesium stearate | 0.1 |
| Third Layer | |

TABLE 3-7-continued

| Blend Composition of Layered Preparation | |
|---|---|
| Blended Ingredients | Blended Amount (mg) |
| Magnesium oxide | 50 |
| Magnesium carbonate | 50 |
| Pregelatinized starch | 30 |
| Corn starch | 10 |
| Anhydrous caffeine | 40 |
| Allylisopropylacetylurea | 30 |
| Magnesium stearate | 1 |
| Total | 425.1 |

TABLE 3-8

| Film Coating Liquid Composition | |
|---|---|
| Blended Ingredients | Blended Amount (g) |
| Hydroxypropylmethylcellulose | 6.0 |
| Macrogol 6000 | 1.2 |
| Titanium oxide | 0.6 |
| Talc | 1.2 |
| Water | 91.0 |
| Total | 100.0 |

Example 3-5 (Stabilized Blend)

240 g of crystalline cellulose are added to 420 g of ibuprofen followed by granulation with an aqueous solution of hydroxypropylcellulose (Freund, Spir a flow model SFC-MINI). 561 g of these granules are weighed followed by the addition of 100 g of carboxymethylcellulose and 3 g of magnesium stearate to produce the first layer.

180 g of allylisopropylacetylurea are added to 210 g of acetaminophen, followed by granulation with an aqueous solution of hydroxypropylcellulose (Freund, Spir a flow model SFC-MINI). 331.5 g of these granules are weighed, followed by the addition of 200 g of anhydrous caffeine, 100 g of carboxymethylcellulose and 4 g of magnesium stearate to produce the second layer.

600 g of magnesium carbonate, 300 g of aluminum glycinate and 180 g of corn starch are mixed followed by the formation of granules with an aqueous gelatin solution (Fukae Powtec, High-Speed Mixer model FS-5). After drying and grading, 930 g of these granules are weighed, followed by the addition of 5 g of magnesium stearate to produce the third layer.

The above-mentioned first through third layers are gradually transferred to a die and formed into tablets to obtain a non-coated layered preparation having the prescription indicated in Table 3-9 below per tablet.

In addition, 1000 g of these tablets are removed and coated with a 4% film with the coating liquid indicated in Table 3-10 below (Freund, Hi-Coater model 300) to obtain a coated layered preparation.

TABLE 3-9

| Blend Composition of Layered Preparation | |
|---|---|
| Blended Ingredients | Blended Amount (mg) |
| First Layer | |
| Ibuprofen | 70 |
| Crystalline cellulose | 40 |
| Hydroxypropylcellulose | 2.2 |
| Carboxmethylcellulose | 20 |
| Magnesium stearate | 0.6 |
| Second Layer | |
| Acetaminophen | 35 |
| Anhydrous caffeine | 40 |
| Allylisopropylacetylurea | 30 |
| Hydroxypropylcellulose | 1.3 |
| Carboxymethylcellulose | 20 |

TABLE 3-9-continued

| Blend Composition of Layered Preparation | |
|---|---|
| Blended Ingredients | Blended Amount (mg) |
| Magnesium stearate | 0.8 |
| Third Layer | |
| Magnesium carbonate | 100 |
| Aluminum glycinate | 50 |
| Gelatin | 6 |
| Corn starch | 30 |
| Magnesium stearate | 1 |
| Total | 446.9 |

TABLE 3-10

| Film Coating Liquid Blend Composition | |
|---|---|
| Blended Ingredients | Blended Amount (g) |
| Hydroxypropylmethylcellulose | 8.0 |
| Macrogol 6000 | 1.6 |
| Titanium oxide | 0.8 |
| Talc | 1.6 |
| Water | 88.0 |
| Total | 100.0 |

Example 3-6 (Stabilized Blend)

120 g of corn starch is added to 420 g of ibuprofen and 210 g of acetaminophen. After kneading with an aqueous solution of hydroxypropylcellulose (Ishiyama Shoten, Kneader), the product is dried and graded, followed by the addition of 3 g of magnesium stearate to 631 g of this product to produce the first layer.

500 g of directly compressive lactose are added to 400 g of anhydrous caffeine and 300 g of allylisopropylacetylurea, followed by mixing and the addition of 12 g of magnesium stearate to produce the second layer.

120 g of corn starch are mixed with 240 g of synthetic hydrotalcite and 240 g of magnesium carbonate, followed by granulation with a gelatin solution (Fukae Powtec, High-Speed Mixer model FS-5). After drying and grading, 566 g of the granules are weighed, followed by the addition of 2.5 g of magnesium stearate to produce the third layer.

The above-mentioned first through third layers are gradually transferred to a die and formed into tablets to obtain a non-coated layered preparation having the prescription indicated in Table 3-11 below per tablet.

In addition, 1000 g of these tablets are removed and coated with a 4% film with the coating liquid indicated in Table 3-12 below (Freund, Hi-Coater model 300) to obtain a coated layered preparation.

TABLE 3-11

| Blend Composition of Layered Preparation | |
|---|---|
| Blended ingredients | Blended Amount (mg) |
| First Layer | |
| Ibuprofen | 70 |
| Acetaminophen | 35 |
| Corn starch | 20 |
| Hydroxypropylcellulose | 1.2 |
| Magnesium stearate | 0.6 |
| Second Layer | |
| Anhydrous caffeine | 40 |
| Allylisopropylacetylurea | 30 |
| Lactose | 50 |
| Magnesium stearate | 1.2 |
| Third Layer | |
| Synthetic hydrotalcite | 40 |
| Magnesium carbonate | 40 |
| Gelatin | 3.2 |

TABLE 3-11-continued

| Blend Composition of Layered Preparation | |
|---|---|
| Blended ingredients | Blended Amount (mg) |
| Corn starch | 30 |
| Magnesium stearate | 0.5 |
| Total | 361.7 |

TABLE 3-12

| Film Coating Liquid Blend Composition | |
|---|---|
| Blended ingredients | Blended Amount (g) |
| Hydroxypropylmethylcellulose | 6.0 |
| Glycerine fatty acid ester | 1.2 |
| Titanium oxide | 0.6 |
| Ethanol | 79.37 |
| Water | 13.83 |
| Total | 100.0 |

Example 3-7 (Stabilized Blend)

240 g of crystalline cellulose are added to 420 g of ibuprofen and 180 g of allylisopropylacetylurea, followed by the formation of granules with an aqueous solution of hydroxypropylcellulose (Freund, Spir a flow model SFC-MINI). 715 g of these granules are weighed, followed by the addition of 100 g of carboxymethylcellulose and 4 g of magnesium stearate to produce the first layer.

175 g of acetoaminophen, 200 g of anhydrous caffeine, 250 g of crystalline cellulose, 100 g of carboxymethylcellulose and 5 g of magnesium stearate are mixed to produce the second layer.

300 g of cumulite (coprecipitate of aluminum hydroxide and sodium bicarbonate), 300 g of magnesium carbonate and 120 g of pregelatinized starch are mixed, followed by granulation with a gelatin solution (Ishivama Shoten, Kneader). After drying and grading, 610 g of these granules are weighed followed by the addition of 3 g of magnesium stearate and mixing to produce the third layer.

The above-mentioned first through third layers are gradually transferred to a die and formed into tablets to obtain a non-coated layered preparation having the prescription indicated in Table 3-13 below per tablet. 1000 g of these tablets are removed and coated with a 4% film with the coating liquid indicated in Table 3-14 below (Freund, Hi-Coater model 300) to obtain a coated layered preparation.

TABLE 3-13

| Blend Composition of Layered Preparation | |
|---|---|
| Blended Ingredients | Blended Amount (mg) |
| First Layer | |
| Ibuprofen | 70 |
| Allylisopropylacetylurea | 30 |
| Crystalline cellulose | 40 |
| Hydroxypropylcellulose | 3 |
| Carboxymethylcellulose | 20 |
| Magnesium stearate | 0.8 |
| Second Layer | |
| Acetaminophen | 35 |
| Anhydrous caffeine | 40 |
| Crystalline cellulose | 50 |
| Carboxyethylcellulose | 20 |
| Magnesium stearate | 1 |
| Third Layer | |
| Cumulite (Kyowa Chemical) | 50 |
| Magnesium carbonate | 50 |
| Gelatin | 2 |
| Pregelatinized starch | 20 |

TABLE 3-13-continued

| Blend Composition of Layered Preparation | |
|---|---|
| Blended Ingredients | Blended Amount (mg) |
| Magnesium stearate | 0.6 |
| Total | 432.4 |

TABLE 3-14

| Film Coating Liquid Blend Composition | |
|---|---|
| Blended Ingredients | Blended Amount (g) |
| Hydroxypropylmethylcellulose | 6.0 |
| Macrogol 6000 | 1.2 |
| Titanium oxide | 0.6 |
| Talc | 1.2 |
| Water | 91.0 |
| Total | 100.0 |

Comparative Example 3-8 (Stabilized Blend)

325 g of ibuprofen, 325 g of acetaminophen, 250 g of magnesium carbonate, 250 g of magnesium oxide and 450 g of corn starch are mixed, followed by kneading with an aqueous solution of hydroxypropylcellulose (Ishiyama Shoten, Kneader). After drying and grading, 999 g of the product are weighed, followed by the addition of 330 g of crystalline cellulose and 6 g of magnesium stearate and mixing. The product is then formed into tablets according to common methods to obtain a non-coated, single layer preparation having the prescription indicated in Table 3-15 below per tablet.

In addition, 1000 g of these tablets are removed and coated with a 4% film with the coating liquid indicated in Table 3-16 below (Freund, Hi-Coater model 300) to obtain a coated, single layer preparation.

TABLE 3-15

| Composition of Single Layer Preparation | |
|---|---|
| Blended Ingredients | Blended Amount (mg) |
| Ibuprofen | 65 |
| Acetaminophen | 65 |
| Magnesium carbonate | 50 |
| Magnesium oxide | 50 |
| Corn starch | 90 |
| Hydroxypropylcellulose | 13 |
| Crystalline cellulose | 110 |
| Magnesium stearate | 2 |
| Total | 445 |

TABLE 3-16

| Film Coating Liquid Blend Composition | |
|---|---|
| Blended ingredients | Blended Amount (g) |
| Hydroxypropylmethylcellulose | 6.0 |
| Macrogol 6000 | 1.2 |
| Titanium oxide | 0.6 |
| Talc | 1.2 |
| Water | 91.0 |
| Total | 100.0 |

Comparative Example 3-9 (Stabilized Blend)

180 g of lactose are added to 390 g of ibuprofen, followed by coating with an aqueous solution of hydroxypropylcellulose (Freund, Spir a flow model SFC-MINI).

390 g of acetaminophen are coated with an aqueous solution of hydroxypropylcellulose (Freund, Spir a flow model SFC-MINI).

180 g of corn starch are added to 300 g of magnesium oxide and 300 g of magnesium carbonate, followed by kneading with an aqueous gelatin solution (Ishiyama Shoten, Kneader). The product is dried and graded to obtain antacid granules.

494 g of the coated ibuprofen, 338 g of the coated acetaminophen, 670 g of the antacid granules, 150 g of allylisopropylacetylurea, 200 g of anhydrous caffeine, 500 g of crystalline cellulose, 250 g of carboxymethylcellulose and 12.5 g of magnesium stearate are mixed. The product is formed into tablets by common methods to obtain a non-coated, single layer preparation having the prescription indicated in Table 3-17 below per tablet.

In addition, 1000 g of these tablets are removed and coated with a 4% film with the coating liquid indicated in Table 3-18 below (Freund, Hi-Coater model 300) to obtain a coated, single layer preparation.

TABLE 3-17

| Composition of Single Layer Preparation | |
|---|---|
| Blended Ingredients | Blended Amount (mg) |
| Ibuprofen | 65 |
| Acetaminophen | 65 |
| Allylisopropylacetylurea | 30 |
| Anhydrous caffeine | 40 |
| Magnesium oxide | 50 |
| Magnesium carbonate | 50 |
| Lactose | 30 |
| Corn Starch | 30 |
| Gelatin | 4 |
| Hydroxypropylcellulose | 6.4 |
| Crystalline cellulose | 100 |
| Carboxymethylcellulose | 50 |
| Magnesium stearate | 2.5 |
| Total | 522.9 |

TABLE 3-18

| Film Coating Liquid Composition | |
|---|---|
| Blended Ingredients | Blended Amount (g) |
| Hydroxypropylmethylcellulose | 9.0 |
| Macrogol 6000 | 1.6 |
| Titanium oxide | 0.9 |
| Talc | 1.6 |
| Water | 88.0 |
| Total | 100.0 |

Comparative Example 3-10 (Stabilized Blend)

390 g of ibuprofen, 390 g of acetaminophen and 180 g of crystalline cellulose are mixed followed by granulation with an aqueous solution of hydroxypropylcellulose (Freund, Spir a flow model SFC-MINI). 816 g of these granules are weighed, followed by the addition of 100 g of carboxymethylcellulose and 5 g of magnesium stearate to produce the first layer.

300 g of magnesium oxide, 300 g of magnesium carbonate and 180 g of corn starch are mixed, followed by the formation of granules with an aqueous gelatin solution (Fukae Powtec, High-Speed Mixer model FS-5). These granules are then dried and graded to produce the second layer.

The above-mentioned first and second layers are gradually transferred to a die and formed into tablets to obtain a non-coated two-layered preparation having the prescription indicated in Table 3-19 below per tablet.

In addition, 1000 g of these tablets are removed and coated with a 4% film with the coating liquid indicated in Table 3-20 below (Freund, Hi-Coater model.300) to obtain a coated, two-layered preparation.

TABLE 3-19

| Composition of Two-Layered Preparation | |
|---|---|
| Blended Ingredients | Blended Amount (mg) |
| First Layer | |
| Ibuprofen | 65 |
| Aceotaminophen | 65 |
| Carboxymethylcellulose | 20 |
| Crystalline cellulose | 30 |
| Hydroxypropylcellulose | 3.2 |
| Magnesium stearate | 1 |
| Second Layer | |
| Magnesium oxide | 50 |
| Magnesium carbonate | 50 |
| Corn starch | 30 |
| Gelatin | 6 |
| Total | 320.2 |

TABLE 3-20

| Film Coating Liquid Blend Composition | |
|---|---|
| Blended Ingredients | Blended Amount (g) |
| Hydroxypropylmethylcellulose | 6.0 |
| Glycerine fatty acid aster | 1.2 |
| Titanium oxide | 0.6 |
| Ethanol | 78.37 |
| Water | 13.83 |
| Total | 100.0 |

TABLE 3-21

| Composition of Two-Layered Preparation | |
|---|---|
| Blended Ingredients | Blended Amount (mg) |
| First Layer | |
| Ibuprofen | 65 |
| Acetaminophen | 65 |
| Allylisopropylacetylurea | 30 |
| Anhydrous caffeine | 40 |
| Lactose | 30 |
| Hydroxypropylcellulose | 5.7 |
| Carboxymethylcellulose | 30 |
| Magnesium stearate | 1.3 |
| Second Layer | |
| Magnesium carbonate | 100 |
| Corn starch | 20 |
| Pregelatinized starch | 20 |
| Total | 407 |

TABLE 3-22

| Film Coating Liquid Blend Composition | |
|---|---|
| Blended Ingredients | Blended Amount (g) |
| Hydroxypropylmethylcellulose | 6.0 |
| Glycerine fatty acid ester | 1.2 |
| Titanium oxide | 0.6 |
| Ethanol | 78.37 |
| Water | 13.83 |
| Total | 100.0 |

Comparative Example 3-11 (Stabilized Blend)

390 g of ibuprofen, 390 g of acetaminophen, 180 g of allylisopropylacetylurea and 180 g of lactose are mixed, followed by the formation of granules with an aqueous solution of hydroxypropylcellulose (Freund, Spir a flow model SFC-MINI). 978.5 g of these granules are weighted, followed by the addition of 200 g of anhydrous caffeine, 150 g of carboxymethylcellulose and 6.5 g of magnesium stearate and mixing to produce the first layer.

600 g of magnesium carbonate, 120 g of corn starch and 120 g of pregelatinized starch are added and mixed, followed by the addition of water and granulation (Fukae Powtec, High-Speed Mixer model FS-5). These granules are then dried and graded to produce the second layer.

The above-mentioned first and second layers are gradually transferred to a die and formed into tablets to obtain a non-coated two-layered preparation having the prescription indicated in Table 3-21 below per tablet.

In addition, 1000 g of these tablets are removed and coated with a 4% film with the coating liquid indicated in Table 3-22 below (Freund, Hi-Coater model 300) to obtain a coated, two-layered preparation.

Each of the non-coated tablet preparations and coated tablet preparations (Examples 3-1 through 3-7 and Comparative Examples 3-8 through 3-11) obtained above were packed in PTP packs (VSS: 250 μm vinyl chloride, single-layer film sealed in aluminum film), and stored at room temperature and 40° C. and 75% RH to examine the stored state after 1 and 3 months. Those results are indicated in Table 3-23 below.

In addition, each of the tablet preparations were similarly packed in PTP packs (VSL: 330 μm vinyl chloride, multi-layered film sealed in aluminum film), and stored at room temperature and 40° C. and 75% RH and at 50° C. and 75% RH to examine the stored state after 1 and 3 months. Those results are indicated in Table 3-24 and Table 3-25 below.

Moreover, each of the tablet preparations were similarly stored in glass bottles. After sealing the bottles, the tablet preparations were stored at room temperature and 40° C. and 75% RH and at 50° C. and 75% RH to examine the stored state after 1 and 3 months. Those results are indicated in Table 3-26 and 3-27 below.

Furthermore, the standards used for evaluation of the state of the preparations after storage are as indicated below.

TABLE 3-23

| | Forced Acceleration Test Package Material: VSS | | | | | | | |
|---|---|---|---|---|---|---|---|---|
| Preparation | Non-coated preparations | | | | Coated preparations | | | |
| Time | After 1 month | | After 3 months | | After 1 month | | After 3 months | |
| Conditions | Room temp. | 40° C. 75% RH | Room temp. | 40° C. 75% RH | Room temp. | 40° C. 75% RH | Room temp. | 40° C. 75% RH |
| Example | | | | | | | | |
| 3-1 | − | − | − | + | − | − | − | − |
| 3-2 | − | − | − | − | − | − | − | − |
| 3-3 | − | − | − | + | − | − | − | − |
| 3-4 | − | − | − | − | − | − | − | − |
| 3-5 | − | − | − | + | − | − | − | − |
| 3-6 | − | − | − | − | − | − | − | − |
| 3-7 | − | − | − | + | − | − | − | − |
| Comp. | | | | | | | | |

TABLE 3-23-continued

Forced Acceleration Test
Package Material: VSS

| Preparation | Non-coated preparations | | | | Coated preparations | | | |
|---|---|---|---|---|---|---|---|---|
| Time | After 1 month | | After 3 months | | After 1 month | | After 3 months | |
| Conditions | Room temp. | 40° C. 75% RH | Room temp. | 40° C. 75% RH | Room temp. | 40° C. 75% RH | Room temp. | 40° C. 75% RH |
| Examples | | | | | | | | |
| 3-8 | +++ | +++ | +++ | +++ | +++ | +++ | +++ | +++ |
| 3-9 | +++ | +++ | +++ | +++ | +++ | +++ | +++ | +++ |
| 3-10 | ++ | +++ | +++ | +++ | + | ++ | +++ | +++ |
| 3-11 | ++ | +++ | +++ | +++ | + | ++ | +++ | +++ |

—: No change
+: Slight coloring
++: Remarkable coloring
+++: Remarkable coloring and deformation

TABLE 3-24

Forced Acceleration Test - Abuse Test
Package Material: VSL
Preparation: Non-coated preparation

| | After 1 month | | | After 3 months | | |
|---|---|---|---|---|---|---|
| Time | | 40° C. | 50° C. | | | |
| Conditions | Room temp. | 75% RH | 75% RH | Room temp. | 40° C. 75% RH | 50° C. 75% RH |
| Example | | | | | | |
| 3-1 | — | — | — | — | — | + |
| 3-2 | — | — | — | — | — | — |
| 3-3 | — | — | — | — | — | + |
| 3-4 | — | — | — | — | — | — |
| 3-5 | — | — | — | — | — | + |
| 3-6 | — | — | — | — | — | — |
| 3-7 | — | — | — | — | — | + |
| Comp. Examples | | | | | | |
| 3-8 | +++ | +++ | +++ | +++ | +++ | +++ |
| 3-9 | +++ | +++ | +++ | +++ | +++ | +++ |
| 3-10 | + | ++ | +++ | ++ | +++ | +++ |
| 3-11 | + | ++ | +++ | ++ | +++ | +++ |

TABLE 3-25

Forced Acceleration Test - Abuse Test
Package Material: VSL
Preparation: Coated preparation

| | After 1 month | | | After 3 months | | |
|---|---|---|---|---|---|---|
| Time | | 40° C. | 50° C. | | | |
| Conditions | Room temp. | 75% RH | 75% RH | Room temp. | 40° C. 75% RH | 50° C. 75% RH |
| Example | | | | | | |
| 3-1 | — | — | — | — | — | + |
| 3-2 | — | — | — | — | — | — |
| 3-3 | — | — | — | — | — | + |
| 3-4 | — | — | — | — | — | — |
| 3-5 | — | — | — | — | — | + |
| 3-6 | — | — | — | — | — | — |
| 3-7 | — | — | — | — | — | + |
| Comp. Examples | | | | | | |
| 3-8 | +++ | +++ | +++ | +++ | +++ | +++ |
| 3-9 | +++ | +++ | +++ | +++ | +++ | +++ |
| 3-10 | + | ++ | +++ | ++ | +++ | +++ |
| 3-11 | + | ++ | +++ | ++ | +++ | +++ |

TABLE 3-26

Forced Acceleration Test - Abuse Test
Package Material: Glass bottle
Preparation: Non-coated preparation

| | After 1 month | | | After 3 months | | |
|---|---|---|---|---|---|---|
| Time | | 40° C. | 50° C. | | | |
| Conditions | Room temp. | 75% RH | 75% RH | Room temp. | 40° C. 75% RH | 50° C. 75% RH |
| Example | | | | | | |
| 3-1 | — | — | — | — | — | — |
| 3-2 | — | — | — | — | — | — |
| 3-3 | — | — | — | — | — | — |
| 3-4 | — | — | — | — | — | — |
| 3-5 | — | — | — | — | — | — |
| 3-6 | — | — | — | — | — | — |
| 3-7 | — | — | — | — | — | — |
| Comp. Examples | | | | | | |
| 3-8 | ++ | +++ | +++ | +++ | +++ | +++ |
| 3-9 | ++ | +++ | +++ | +++ | +++ | +++ |
| 3-10 | + | ++ | +++ | ++ | +++ | +++ |
| 3-11 | + | ++ | +++ | ++ | +++ | +++ |

TABLE 3-27

Forced Acceleration Test - Abuse Test
Package Material: Glass bottle
Preparation: Coated preparation

| | After 1 month | | | After 3 months | | |
|---|---|---|---|---|---|---|
| Time | | 40° C. | 50° C. | | | |
| Conditions | Room temp. | 75% RH | 75% RH | Room temp. | 40° C. 75% RH | 50° C. 75% RH |
| Example | | | | | | |
| 3-1 | — | — | — | — | — | — |
| 3-2 | — | — | — | — | — | — |
| 3-3 | — | — | — | — | — | — |
| 3-4 | — | — | — | — | — | — |
| 3-5 | — | — | — | — | — | — |
| 3-6 | — | — | — | — | — | — |
| 3-7 | — | — | — | — | — | — |
| Comp. Examples | | | | | | |
| 3-8 | ++ | +++ | +++ | +++ | +++ | +++ |
| 3-9 | ++ | +++ | +++ | +++ | +++ | +++ |
| 3-10 | + | ++ | +++ | ++ | +++ | +++ |
| 3-11 | + | ++ | +++ | ++ | +++ | +++ |

Although the non-coated preparations consisting of layers of ibuprofen, acetaminophen and antacid in forced acceleration testing (40° C., 75% RH, 3 months, vinyl chloride, single-layer film: VSS), and coated preparations in abuse testing (50° C., 75% RH, 3 months, vinyl chloride, multi-layer film: VSL) demonstrated slight coloring, such discoloration was not of an extent that impairs product value. Furthermore, there were no changes at all in other tests. Thus, a layered preparation having a layer having ibuprofen as the main ingredient, a layer having an antacid as the main ingredient, and a layer between the above two layers not containing both of the above substances, and containing acetaminophen in a layer other than the layer having antacid as the main ingredient, was stable and free of the occurrence of remarkable changes regardless of whether coated or not. In addition, since the coated preparation does not demonstrate any changes whatsoever in force acceleration testing even in the case of using vinyl chloride single-layered film (VSS), this indicated that coating results in an even greater improvement in stability.

We claim:

1. An ibuprofen-containing antipyretic analgesic preparation comprising a layer containing ibuprofen as the main ingredient and not containing antacids, a layer containing a magnesium-based antacid as the main ingredient and not containing ibuprofen, and at least one layer between the above layers that does not contain either of the above ingredients, wherein acetaminophen is contained in a layer other than the layer containing the antacid as the main ingredient, the acetaminophen content of the preparation being 0.01–30 parts by weight based on 1 part by weight of ibuprofen, and the magnesium-based antacid content of the preparation being 0.05–100 parts by weight based on 1 part by weight of the total amount of ibuprofen and acetaminophen.

2. A preparation as claimed in claim 1, wherein the magnesium-based antacid is at least one compound selected from the group consisting of magnesium silicate, magnesium oxide, magnesium hydroxide, magnesium carbonate, exissicated mixed aluminum hydroxide and magnesium carbonate gel, the coprecipitation product of aluminum hydroxide, calcium carbonate and magnesium carbonate, magnesium metasilicate aluminate, magnesium aluminosilicate, and the coprecipitate of magnesium hydroxide and potassium aluminum sulfate.

3. An ibuprofen-containing antipyretic analgesic preparation comprising ibuprofen, acetaminophen and at least one sedative selected from the group consisting of bromovalerylurea and allylisopropylacetylurea, the acetaminophen content being 0.01–30 parts by weight based on 1 part of ibuprofen, and the sedative content being 0.01–30 parts by weight based on 1 part of ibuprofen.

4. A preparation as claimed in claim 3, wherein the above-mentioned preparation contains 0.05–100 parts by weight of a magnesium-based antacid based on 1 part by weight of the total amount of ibuprofen and acetaminophen.

5. A preparation as claimed in claim 1, wherein the above-mentioned preparation is coated.

* * * * *